US007902142B2

(12) United States Patent
Fukuda et al.

(10) Patent No.: US 7,902,142 B2
(45) Date of Patent: Mar. 8, 2011

(54) FRAGRANCE COMPOSITION

(75) Inventors: Kazuyuki Fukuda, Sumida-ku (JP); Naotoshi Toki, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/994,420

(22) PCT Filed: Jul. 24, 2006

(86) PCT No.: PCT/JP2006/314567

§ 371 (c)(1),
(2), (4) Date: Jan. 2, 2008

(87) PCT Pub. No.: WO2007/013394

PCT Pub. Date: Feb. 1, 2007

(65) Prior Publication Data

US 2009/0123404 A1 May 14, 2009

(30) Foreign Application Priority Data

Jul. 25, 2005 (JP) ................................ 2005-213659

(51) Int. Cl.
*A61K 8/18* (2006.01)
*A61Q 13/00* (2006.01)
*C07C 35/00* (2006.01)
*A61K 8/00* (2006.01)

(52) U.S. Cl. .................. 512/19; 512/1; 512/17; 568/819

(58) Field of Classification Search .................... 512/17, 512/1, 19; 568/819
See application file for complete search history.

(56) References Cited

U.S. PATENT DOCUMENTS 3,718,698 A * 2/1973 Hall ............................. 568/342
4,406,828 A * 9/1983 Gonzenbach et al. .......... 512/17
4,872,917 A * 10/1989 Howe et al. ................... 131/275

FOREIGN PATENT DOCUMENTS

CN 1127778 A 7/1996

OTHER PUBLICATIONS

Corbier et al. Flavors and Fragrances A world Perspective pp. 483-494; Proceedings of the 10th International Congress of Essential Oils 11-16-20 1986 Washington DC, USA.*
Shah N. www chem wisc edu areas organic studsemin shah shah-abs pdf.pdf 2002.*
Ohloff et al. Coatica Chemica Acta vol. 58 No. 4 pp. 491-509 1985.*
Wood and Cellulosic Chemistry 2nd ed. David Hon et al. p. 251.*
1194420-Search, Mar. 4, 2009, 8-drimanol chemical search results.*
Corbier et al., "New Components from French Tobacco Absolute (*Nicotiana tabacum*)", Flavors and Fragrances: A World Perspective, pp. 483-494, 1988.
Ohloff, Günther et al., "Structure-Activity Relationships in Odor Perception of Drimane Derivatives", Croatica Chemica Acta, vol. 58, No. 4, pp. 491-509, 1985.
U.S. Appl. No. 11/911,751, filed Oct. 17, 2007, Toki et al.
Joseph R. Hlubucek, et al., "Tobacco Chemistry. 25. Two New Drimane Sesquiterpene Alcohols from Greek *Nicotiana tabacum* L.", Acta Chemica Scandinavica, B 28, No. 3, 1974, pp. 289-294.
Curt R. Enzell, et al., "Tobacco Chemistry 81. Biotransformations of (Z)-Abienol using Plant Cell Cultures of *Nicotiana silvestris*", Acta Chemica Scandinavica, vol. 49, 1995, pp. 375-379.
U.S. Appl. No. 12/539,257, filed Aug. 11, 2009, Toki et al.
S. Arctander, *Perfume and Flavor Materials of Natural Origin,* Elizabeth, N.J. 1960, pp. 617-620.
Office Action issued Jul. 30, 2010, in Chinese Patent Application No. 200680024188.7, filed Dec. 31, 1988 (with English-language Translation).
Office Action issued Sep. 14, 2010, in Japanese Patent Application No. 2005-213659, filed Jul. 25, 2005 (w/English Translation).
Registry No. 53163-43-2 (STN).
Office Action issued Jul. 30, 2010, in Chinese Patent Application No. 200680024188.7, filed Dec. 31, 1988 (with English-language Translation).

* cited by examiner

*Primary Examiner* — Milton I Cano
*Assistant Examiner* — Aaron Greso
(74) *Attorney, Agent, or Firm* — Oblon, Spivak, McClelland, Maier & Neustadt, L.L.P.

(57) ABSTRACT

Provided is a fragrance composition containing 8- drimanol represented by the formula (Ia):

(1a)

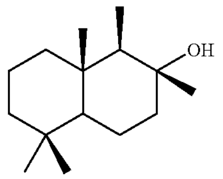

and containing none of 7-acetyl-1,2,3,4,5,6,7,8-octahydro-1,1,6,7-tetramethylnaphthalene, 1,2,3,4,4a,5,6,7-octahydro-2,5,5-trimethyl-2-naphthalenol, 1,2,3,4,4a,7,8,8a- octahydro-2,4a,5,8a-tetramethyl-l-naphthylformate, 3a-ethyl-dodecahydro-6, 6,9a-trimethylnaphtho[2,1-b]furan, and racemic and optically-active substance of dodecahydro- 3a,6, 6,9a-tetramethylnaphtho[2,1-b]furan; and personal care products, household products and environmental hygiene products containing the composition. The fragrance composition of the present invention contains 8-drimanol (Ia) so that it can produce various novel odors and emit a odor with softness and warmth typical to natural ambergris.

18 Claims, No Drawings

FRAGRANCE COMPOSITION

CROSS REFERENCES TO RELATED APPLICATIONS

This application is a 371 of International Patent Application No. PCT/JP06/314567, filed on Jul. 24, 2006, and claims priority to Japanese Patent Application No. 2005-213659, filed on Jul. 25, 2005.

FIELD OF THE INVENTION

The present invention relates to a fragrance composition containing a decalin alcohol having a specific structure.

BACKGROUND OF THE INVENTION

Fragrances contained in personal care products or household products not only produce a pleasant smell during their use but also play a role in heightening the functions of these products, for example, comfort and refreshed feeling after shampooing or washing with them. In compounding fragrances, therefore, fragrance compositions which are favored highly and can satisfy the functions of the individual products are created by carefully selecting synthetic fragrances or natural fragrances with a good smell and in addition, by using in combination fragrance compounds showing various behaviors in diffusiveness and substantivity, depending on the using scenes of them.

Since there is an increasing demand for natural-odor rich and long lasting fragrance compounds, novel compounds releasing a woody-amber odor have been searched while paying attention to those having a odor of high quality with softness or warmth typical to natural ambergris, those having a powerful odor and therefore effective even by the addition of a small amount, and those showing high adsorption to clothes or hair and high substantivity. As one example of fragrance compounds with a powerful odor, 1,2,3,4,4a,5,6,7-octahydro-2,5,5-trimethyl-2-naphthalenol can be given. Although the compound gives a odor of animalistic warmth, too intense odor hinders its use for lightly fragranced cosmetics which are applied directly to the skin and in addition, it may impair the odors of other fragrance compounds.

The substantivity of a odor may be enhanced by increasing the molecular weight of a fragrance compound, thereby controlling its volatility. For example, hexahydro-1', 1', 5',5'-tetramethylspiro[1,3-dioxolane-2,8'(5'H)-[2H-2,4a]-methanonaphthalene which is a cyclic isolongifolanone ketal has higher substantivity than isolongifolanone, but an increase in the molecular weight weakens its smell, leading to loss of a woody, soft and natural odor typical to isolongifolanone.

There is accordingly a demand for the development of, as fragrance compounds having a woody-amber odor, natural-odor rich ones having a high quality and producing a long-lasting odor with adequate intensity depending on various product forms or using scenes.

As a result of attention to the steric structure of a decalin skeleton and methyl groups attached thereto and investigation on the synthesis of a decalin alcohol highly substituted with methyl groups, G. Ohloff et al. have reported that 9-nordrimanol having four methyl groups produces an excellent amber odor. Those having at least five methyl groups as substituents or those having an ethyl group introduced therein were however odorless or attracted no attention (Non-patent document 1). For example, 8-drimanol having a steric structure of the following formula (1a) did not become the object of the investigation in the study of G. Ohloff, et al. made on fragrance compounds having a decalin skeleton. Non-patent document 1 does not include a description on the odor of driman-8β-ol but includes only a description that (9βH)-driman-8β-ol different in the steric structure is odorless. None of the above-described compounds has been used in practice as a fragrance because no industrial production process of them has been found as yet.

(1a)

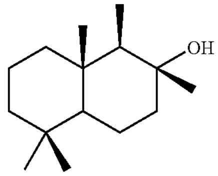

J. R. Hlubucek found that *Nicotiana tabacum* L. of Greek tobacco contains the compound represented by the formula (1a) and tried to produce it from drim-7-en-11-ol, but did not describe the odor of such a compound. The importance of the compound as a fragrance has therefore not been known (Non-patent document 2).

C. R. Enzell succeeded in preparing a mixture containing 8-drimanol by bioconversion of (Z)-abienol, but did not describe the compound as a fragrance (Non-patent document 3).

[Non-patent Document 1] *Croatica Chemica Acta,* 58 (4) p.491 (1985)
[Non-patent Document 2] *Acta Chemica Scandinavica B* 28 No.3 p.289 (1974)
[Non-patent Document 3] *Acta Chemica Scandinavica* 49 p.375 (1995)

DISCLOSURE OF THE INVENTION

In one aspect of the present invention, there is provided a fragrance composition containing 8-drimanol represented by the formula (1a) and containing none of 7-acetyl-1,2,3,4,5,6,7,8-octahydro-1,1,6,7-tetramethylnaphthalene, 1,2,3,4,4a,5,6,7-octahydro-2,5,5-trimethyl-2-naphthalenol, 1,2,3,4,4a,7,8,8a-octahydro-2,4a,5,8a-tetramethyl-1-naphthylformate, 3a-ethyldodecahydro-6,6,9a-trimethylnaphtho[2,1-b]furan, and racemic and optically-active substance of dodecahydro-3a,6,6,9a-tetramethylnaphtho[2,1-b]furan.

(1a)

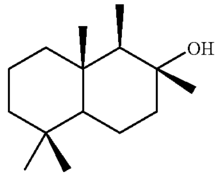

In another aspect of the present invention, there is also provided a personal care product, household product and environmental hygiene product each containing the fragrance composition.

In a further aspect of the present invention, there is also provided a method of adding 8-drimanol represented by the formula (1a) to a fragrance composition for improving the odor thereof.

MODE FOR CARRYING OUT THE INVENTION

The present invention relates to a fragrance composition having adequate intensity and substantivity, can exhibit an effect for heightening warmth and quality peculiar to natural ambergris even by the addition of a small amount, and has high versatility.

The present inventors have found that 8-drimanol represented by the formula (1a) (which will hereinafter be called "8-drimanol (1a)") which so far has not been used as a fragrance has a characteristic that it not only has a weak woody amber odor at room temperature but also releases a strong amber odor when heated to a body temperature or higher.

Moreover, the present inventors have found that 8-drimanol (1a) used in combination with another fragrance compound is effective for imparting thereto softness and warmth like those of natural ambergris, heightening the quality of fragrance and accelerating its intensity; that when a fragrance composition containing the decalin alcohol is added to personal care products or household products, 8-drimanol (1a) emits a moderate level of an amber odor under heated conditions, for example, during bathing, during hair blowing or immediately after drying clothes or by a body temperature and leaves a comfortable odor on the skin, hair or clothes to which it is applied; and that 8-drimanol (1a) is a fragrance compound having an odor strong enough not to upset the fragrance balance of the fragrance composition even when it is added either in a small amount or large amount, having sufficient substantivity depending on the using scene of products and having high versatility.

The 8-drimanol (1a) contained in the fragrance composition of the present invention itself has a weak woody amber odor. Combined use of 8-drimanol (1a) with another fragrance makes it possible to prepare a fragrance composition emitting a soft and warm odor typical to natural ambergris and keep its odor for a long period of time with adequate intensity. In other words, the fragrance of a fragrance composition can be improved by the addition of 8-drimanol (1a) thereto.

As a preparation process of 8-drimanol (1a), a process using the above-described drim-7-en-11-ol as a raw material (Non-patent document 2) is known, but this process needs as a starting raw material a compound not easily available and requires even 6 steps for the preparation (Non-patent document 2). It is therefore preferred to prepare it by a preparation process of decalin alcohol (1) represented by the following reaction scheme which utilizes the decarbonylation reaction of hemiacetal (2) or aldehyde (3). This process enables efficient preparation of decalin alcohol (1) in short steps.

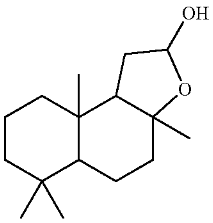

(2)

or

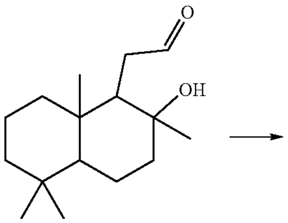

(3)

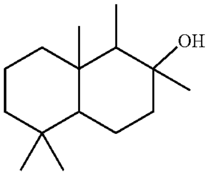

(1)

Conversion of Hemiacetal (2) or Aldehyde (3) to Decalin Alcohol (1)

Preparation of decalin alcohol (1) by decarbonylation reaction of hemiacetal (2) or aldehyde (3) according to the present invention can be performed by a reaction using a transition metal complex. Hemiacetal (2) and aldehyde (3) may be used either singly or in combination.

As the transition metal complex, rhodium complexes, ruthenium complexes and iron complexes are preferred, rhodium complexes being more preferred. Of these, halotris (triphenylphosphine)rhodium (I), halocarbonylbis(triphenylphosphine)rhodium (I) are preferred, of which chlorotris (triphenylphosphine)rhodium (I); $[RhCl(PPh_3)_3]$, chlorocarbonylbis(trisphenylphosphine)rhodium (I); $[RhCl(CO)(PPh_3)_2]$ and the like are more preferred.

The amount of the transition metal complex is preferably from 1 to 20 moles per mole of the total amount of hemiacetal (2) and aldehyde (3), with the amount from 1 to 2 moles being more preferred.

Addition of an adequate amount of a bidentate phosphine ligand to the rhodium complex can drastically reduce the amount of the rhodium complex and enables the reaction at a catalytic amount of it. Examples of the bidentate phosphine ligand include 1,2-bis(diphenylphosphino)ethane, 1,3-bis (diphenylphosphino)propane and 1,4-bis(diphenylsphosphino)butane. Of these, 1,3-bis(diphenylphosphino)propane is more useful.

The amount of the bidentate phosphine ligand, if it is added, is preferably from 1 to 50 moles, more preferably from 1 to 4 moles per mole of the rhodium complex. The amount of the rhodium complex is preferably from 0.00001 to 1 mole per mole of the total amount of hemiacetal (2) and aldehyde (3), of which an amount of from 0.001 to 0.05 mole is more preferred from the viewpoints of economy and productivity.

The rhodium complex and bidentate phosphine ligand may be added intermittently with the progress of the reaction. The rhodium complex and the bidentate phosphine ligand may be added separately or the rhodium complex having the ligand coordinated thereto in advance may be used.

As a reaction solvent, halogen-containing solvents and aromatic solvents such as dichloromethane, benzene, toluene and xylene are preferred. In the reaction using a catalytic amount of the rhodium complex, xylene which enables a high-temperature reaction is more useful. The amount of the solvent is preferably from 1 to 100 mL per g of the total amount of hemiacetal (2) and aldehyde (3). From the viewpoint of productivity, an amount from about 1 to 10 mL is preferred.

The transition metal complex is reacted with hemiacetal (2) or aldehyde (3) preferably in an inert gas atmosphere such as a nitrogen gas or argon gas. The reaction temperature may be any temperature insofar as it is not too high. A temperature from 20 to 120° C. is preferred. The reaction using a catalytic amount of the rhodium complex is performed preferably in a reflux of the solvent under circulation of a nitrogen gas in order to discharge carbon monoxide out of the system in this reaction. The reaction temperature is therefore set at around the boiling point of the solvent.

The terminal point of the present reaction is a time when disappearance of hemiacetal (2) or aldehyde (3) is confirmed by gas chromatography, thin-layer liquid chromatography or the like. The reaction time is typically from 1 to 24 hours.

Conversion from Sclareolide (4) to Hemiacetal (2) and Aldehyde (3)

Hemiacetal (2) and aldehyde (3) used in the above reaction can be prepared by reducing a sclareolide (4).

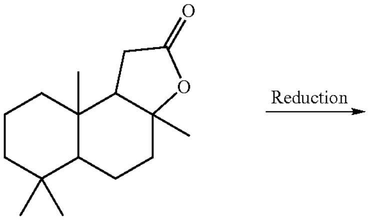

(4)

-continued

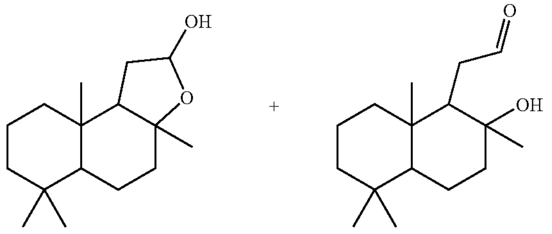

(2) (3)

As the reducing agent, metal hydrides are preferred, with aluminum hydride being more preferred. The amount of the reducing agent is preferably from 0.1 to 5 moles, more preferably from 0.5 to 2 moles, per mole of the sclareolide (4).

As the solvent, solvents having a low solidifying point, for example, dichloromethane, hexane and toluene are preferred. Of these, anhydrous solvents are more preferred.

The reducing agent is reacted with the sclareolide (4) preferably in an inert gas atmosphere such as nitrogen gas or argon gas under anhydrous conditions. The reaction temperature is preferably low, with that from −78 to 40 ° C. being more preferred.

The terminal point of the present reaction is a time when disappearance of the sclareolide (4) is confirmed by gas chromatography, thin-layer liquid chromatography or the like. The reaction time is typically from 30 minutes to 2 hours.

In the process of the present invention, when (+)-sclareolide (4a) available by the oxidation of (−)-sclareol which is an extract of natural clary sage is used as the sclareolide (4), 8-drimanol (1a) can be obtained as the decalin alcohol (1). The resulting 8-drimanol (1a) is not known to be useful as a fragrance, but it has a characteristic that a weak amber odor at room temperature becomes a strong and distinctive amber odor at a temperature from body temperature to 50° C.

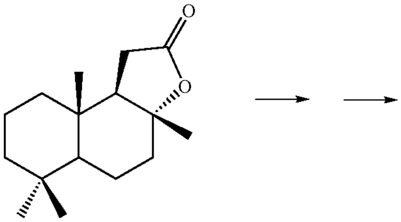

(+)-sclareolide (4a)

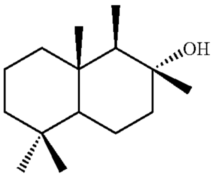

8-drimanol (1a)

Heating of (+)-sclareolide (4a) in formic acid in the presence of concentrated sulfuric acid can yield 9-epi-sclareolide (4c) (Non-patent Document 1). By the reaction of the present invention using this epi-sclareolide, (9βH)-driman-8-ol (1d) can be obtained. Since the compound thus obtained has a hydroxy group in an equatorial position and is similar to 8-drimanol (1a) in a steric structure, it has an amber odor.

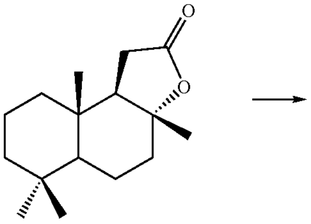

(+)-sclareolide (4a)

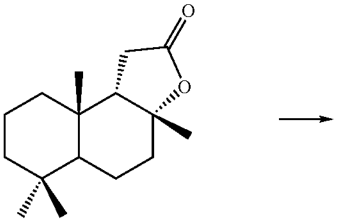

9-epi-sclareolide (4c)

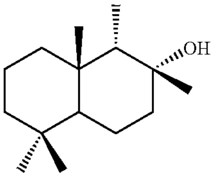

(9βH)-driman-8α ol (1d)

Use of isosclareolide (4d) as the sclareolide (4) can yield driman-8β-ol (1b).

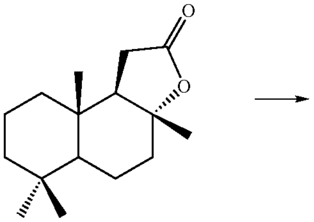

isosclareolide (4d)

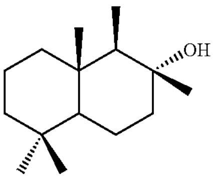

driman-8β-ol (1b)

As the sclareolide (4), a mixture may be used. From (±)-sclareolides (4ab) obtained from homofarnesylic acid in a known manner (International Patent Publication No. Hei 8-506103), a mixture containing 8-drimanol (1a) can be prepared at a lower cost.

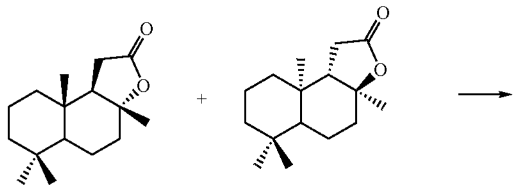

(±)-sclareolides (4ab)

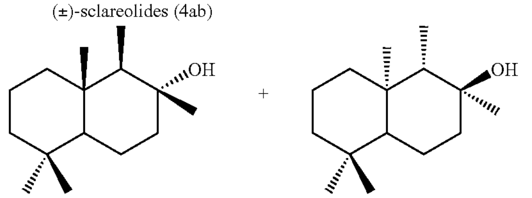

mixture containing 8-drimanol (1a)

The fragrance composition of the present invention may contain not only 8-drimanol (1a) but also one or more fragrance substances, for example, as shown below in combination.

(1) Hydrocarbons such as limonene, α-pinene, β-pinene, terpinene, cedrene, longifolene and valencene.

(2) Alcohols such as linalool, citronellol, geraniol, nerol, terpineol, dihydromyrcenol, ethyl linalool, farnesol, nerolidol, cis-3-hexenol, cedrol, menthol, borneol, phenyl ethyl alcohol, benzyl alcohol, phenyl hexanol, 2,2,6-trimethyl cyclohexyl-3-hexanol, 1-(2-t-butyl cyclohexyloxy)-2-butanol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, 3-methyl-5-(2,2,3-trimethyl-3-cyclopenten-1-yl)-pentan-2-ol, 2-methyl-4-(2,2,3-trimethyl-3-cyclopenten-1-yl)-butanol, 3,3-dimethyl-5-(2,2,3-trimethyl-3-cyclopenten-1-yl)-4-penten-2-ol, 3-methyl-5-(2,2,3-trimethyl-3-cyclopenten-1-yl)-4-penten-2-ol, isocamphyl cyclohexanol and 3,7-dimethyl-7-methoxyoctan-2-ol.

(3) Phenols such as eugenol, thymol and vanillin.

(4) Esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styrallyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl 2-cyclohexylpropionate, benzyl propionate, citronellyl butyrate, dimethylbenzylcarbinyl n-butyrate, tricyclodecenyl isobutyrate, methyl 2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyl dihydrojasmonate, methyl 2,4-dihydroxy-3,6-dimethyl benzoate, ethylmethylphenyl glycidate, methyl anthranilate, and FRUITATE (trade name, product of Kao).

(5) Aldehydes such as n-octanal, n-decanal, n-dodecanal, 2-methylundecanal, 10-undecenal, citronellal, citral, hyroxycitronellal, dimethyltetrahydrobenzaldehyde, 4(3)-(4-hydroxy-4-methylpentyl)-3-cyclohexene-1-carboaldehyde,2-cyclohexylpropanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde.

(6) Ketones such as methyl heptenone, 4-methylene-3,5,6,6-tetramethyl-2-heptanone, amyl cyclopentanone, 3-methyl-2-(cis-2-penten-1-yl)-2-cyclopenten-1-one, methyl cyclopentenolone, rose ketone, γ-methylionone, α-ionone, carvone, menthone, camphor, nootkatone, benzyl acetone, anisyl acetone, methyl β-naphthyl ketone, 2,5-dimethyl-4-hydroxy-3(2H)-furanone, maltol, muscone, civetone, cyclopentadecanone and cyclohexadecenone.

(7) Acetals and ketals such as acetaldehyde ethyl phenyl propyl acetal, citral diethyl acetal, phenylacetaldehyde glycerin acetal and ethyl acetacetate ethylene glycol ketal.

(8) Ethers such as anethole, β-naphthyl methyl ether, β-naphthyl ethyl ether, limonene oxide, rose oxide, and 1,8-cineol; and nitriles such as geranylnitrile and citronellylnitrile.

In addition to the carboxylic acids, there can be also used, in combination with decalin alcohol (1), lactones such as γ-nonalactone, γ-undecalactone, δ-decalactone, γ-jasmolactone, coumarin, cyclopentadecanolide, cyclohexadecanolide, ambrettolide, ethylene brassylate and 11-oxahexadecanolide; and natural essential oils and natural extracts of orange, lemon, bergamot, mandarin, peppermint, spearmint, lavender, chamomile, rosemary, eucalyptus, sage, basil, rose, geranium, jasmine, ylang-ylang, anis, clove, ginger, nutmeg, cardamom, cedar, Japanese cypress, vetiver, patchouli, and labdanum.

In the fragrance composition of the present invention, any combination of 8-drimanol (1a) and another fragrance selected from the above-described ones is usable. Their mixing ratio is not particularly limited, but a woody amber odor having softness and warmth peculiar thereto can be produced by adjusting the content of 8-drimanol (1a) in the fragrance composition to preferably from 0.0001 to 99 mass %, more preferably from 0.01 to 50 mass %.

The fragrance composition of the present invention can be incorporated in or used for fragrant products having various forms. Examples of the field to which the fragrance composition of the present invention can be applied include personal care products, household products, and environmental hygiene products.

The "personal care products" are products for keeping the appearance of a person clean or beautiful. Specific examples include soaps, body shampoos, hair shampoos, hair care products, cosmetics (for instance, skin care products, make-up and the like), perfumes, eau de colognes, antiperspirants, deodorants, and bath agents.

The "household products" are products for keeping the functions or cleanness of homes and various products such as household commodities necessary for home life. Specific examples include fabric detergents, fabric softeners, fabric starches, house cleaners, bathroom cleaners, dishwashing detergents, bleaching agents, mildew cleaners and floor waxes.

The "environmental hygiene products" are products for controlling the environment to a desired condition or atmosphere. Specific examples of the products containing the fragrance composition to control the fragrance emitted to the environment include air fresheners, deodorants, incense, incense sticks and candles.

Although 8-drimanol (1a) has a weak woody amber odor at room temperature, it drastically increases intensity of its odor by heating to a body temperature or higher and produces a comfortable amber odor. The fragrance composition of the present invention is therefore highly effective for the sense of smell when they are in product forms to be applied directly to skin or hair, for example, perfumes, eau de colognes, skin care products, cosmetic products and hair care products for beautifying or styling hair and in product forms which need heat during or after treatment therewith, for example, bath agents used under heated atmosphere, hair care products such as shampoo and conditioner which are exposed to heat of a hair drier after use, and products such as fabric conditioners and softeners which are heated after use by a drier or iron.

Since 8-drimanol (1a) has high substantivity, it can leave a delicate soft odor on the skin or hair by direct application. In household products such as fabric detergents and fabric softeners containing it, it can also leave this odor on clothes washed or treated with them. It tends to harmonize well with a fragrance used for environmental hygiene products such as air fresheners, deodorants, incense, incense sticks and candles.

The products containing the fragrance composition of the present invention can be used in various methods. For example, perfumes or cosmetics are aggressively applied to a desired site of a body to emit their odor. Detergents leave their odor, after rinsing, on a site to which they are applied. Air fresheners volatilize and spread their odor in the air. Incense sticks or candles are burnt to release their odor in the air.

As one example of use, addition of 0.5 mass % of a floral-musk type fragrance composition containing 1 mass % of 8-drimanol (1a) to a hair shampoo can produce a soft and warm odor typical to natural ambergris and provide a soft and decent odor to the hair continuously.

EXAMPLES

Referential Example 1

Synthesis of 8-Drimanol (1a) and Evaluation of Its Odor

[Synthesis]

A 200-mL four-neck flask equipped with a stirrer and a thermometer was charged with 5 g of sclareolide and 60 mL of anhydrous dichloromethane in a nitrogen atmosphere. The mixture was cooled to −78° C. while stirring. An n-hexane solution (22 mL) of diisobutylaluminum hydride was slowly added dropwise to the reaction mixture through a syringe, followed by stirring for 25 minutes under cooling. An aqueous saturated solution (12.5 mL) of ammonium chloride was then added in portions and the resulting reaction mixture was heated to room temperature while stirring. After dilution of the resulting solution with diethyl ether, the diluted solution was stirred for 1.5 hours. Anhydrous magnesium sulfate was added. After stirring for a while, the reaction mixture was filtered through Celite. The filtrate was concentrated by removing the solvent under reduced pressure to yield 4.75 g (yield: 95%) of white crystals.

Next, 2 g of the resulting solid was dissolved in 320 mL of dichloromethane in a 1-L four-neck flask and the resulting solution was stirred for several minutes. Chlorotris(triphenylphosphine)rhodium (I) (7.5 g) was added to the resulting solution, followed by stirring for 13 hours under reflux conditions. After the temperature of the solution was returned to room temperature and stirring was conducted for further 30 minutes, the reaction mixture was filtered. The filtrate was concentrated by removing the solvent under reduced pressure and then, purified by silica gel column chromatography (dichloromethane:methanol=100:1, volume ratio) to yield 1.2 g (yield: 60%) of 8-drimanol (1a).

[Evaluation of Odor]

A sheet of aluminum foil was spread over a hot plate and 0.1 g of decalin alcohol (1) obtained by the above-described method was placed on the sheet of aluminum foil. The odor of it was evaluated while raising the temperature, resulting in the following:

Room temperature: a weak woody odor
40° C.: appearance of an amber odor
50° C.: strong amber odor with sweetness
60° C.: a very powerful amber odor

EXAMPLE 1

Fragrance Composition for Perfume

A fragrance composition characterized by a fruity top note after application and remaining of a musk-like softness and at the same time, bright and elegant amber odor on the skin was obtained by adding 0.5 part by mass of 8-drimanol (1a) to 99.5 parts by mass of a fragrance composition formulated as shown in Table 1.

TABLE 1

| Components | Parts by mass. |
|---|---|
| Methyl dihydrojasmonate | 25 |
| 1,3,4,6,7,8-Hexahydro-4,6,6,7,8,8-hexamethylcyclopenta-γ-2-benzopyrane | 15 |
| p-t-Butyl-α-methylhydrocinnamic aldehyde | 8 |
| Orange oil | 5 |
| Ethyl linalool | 4 |
| cis-3-Hexenyl salicylate | 3 |
| Ethylene brassylate | 3 |
| 4(3)-(4-Hydroxy-4-methylpentyl)-3-cyclohexene-1-carboxyaldehyde | 3 |
| Piperonal | 2 |
| Hexyl acetate | 2 |
| Citronellol | 1 |
| Phenylethyl alcohol | 1 |
| 7-Hexadecen-16-olide | 1 |
| Allyl heptanoate | 1 |
| Dihydromyrcenol | 1 |
| p-t-Butylcyclohexyl acetate | 1 |
| 2-t-Butylcyclohexyl ethyl carbonate | 0.5 |
| 3,6-Dimethyl-3-cyclohexene-1-carboaldehyde | 0.2 |
| γ-Undecalactone | 0.2 |
| Styrallyl acetate | 0.2 |
| n-Decanal | 0.1 |
| Rose oxide | 0.1 |
| Dipropylene glycol | 22.2 |
| Total | 99.5 |

EXAMPLE 2

Fragrance Composition for Shampoo

A fragrance composition for shampoo having ambergris and sandalwood odors in harmony and therefore producing a soft odor with sweetness and warmth was obtained by adding 5 mass % of 8-drimanol (1a) to 95 parts by mass of a fragrance composition formulated as shown in Table 2.

TABLE 2

| Components | Parts by mass |
|---|---|
| Linalool | 15 |
| Cyclopentadecanolide | 12 |
| Methyl dihydrojasmonate | 12 |
| p-t-Butyl-α-methylhydrocinnamic aldehyde | 10 |

TABLE 2-continued

| Components | Parts by mass |
|---|---|
| cis-3-Hexenyl salicylate | 10 |
| Dimethylbenzylcarbinyl acetate | 5 |
| Citronellol | 5 |
| Phenylethyl alcohol | 5 |
| 2-Methyl-4-(2,2,3-trimethyl-3-cyclopenten-1-yl)-2-buten-1-ol | 5 |
| α-n-Hexylcinnamic aldehyde | 4 |
| Benzyl acetate | 4 |
| Orange oil | 3 |
| Linalyl acetate | 3 |
| α-Methylionone | 2 |
| Total | 95 |

EXAMPLE 3

Fragrance Composition for Fabric Detergent

A fragrance composition for fabric detergent having, in harmony, a warm odor typical to ambergris and a soft odor typical to sandalwood and producing a jasmine/muguet odor was obtained by adding 5 mass % of 8-drimanol (1a) to 95 parts by mass of a fragrance composition formulated as shown in Table 3.

TABLE 3

| Components | Parts by mass |
|---|---|
| Orange oil | 20 |
| Methyl dihydrojasmonate | 15 |
| Linalool | 10 |
| Cyclopentadecanolide | 10 |
| p-t-Butyl-α-methylhydrocinnamic aldehyde | 10 |
| α-n-Hexylcinnamic aldehyde | 8 |
| Citronellol | 6 |
| Isocamphyl cyclohexanol | 6 |
| γ-Methylionone | 3 |
| o-t-Butylcyclohexyl acetate | 3 |
| 2-Methyl-4-(2,2,3-trimethyl-3-cyclopenten-1-yl)-2-buten-1-ol | 3 |
| Methyl β-naphthyl ketone | 0.5 |
| Dipropylene glycol | 0.5 |
| Total | 95 |

EXAMPLE 4

Fabric Detergent Composition

To 99.6 parts by mass of a powdery detergent composition formulated as shown in Table 4, 0.4 parts by mass of the fragrance composition for fabric detergent (Table 3) obtained in Example 3 was sprayed. A 20 g portion of the resulting detergent was weighed and dissolved in 30 L of 3.5° DH hard water. A commercially available cotton towel (2 kg) was dipped in the resulting aqueous solution. After stirring for 5 minutes and rinsing for 1 minute, the towel was dehydrated. As a result of evaluation of the odor of the cotton towel, it produced a odor with softness and cleanliness. The cotton towel immediately after heating and drying in a drier produced a characteristic odor with warmth typical to ambergris.

TABLE 4

| Components | Parts by mass |
|---|---|
| Linear sodium alkyl ($C_{10}$-$C_{18}$) benzene sulfonate | 30 |
| Sodium alkyl ($C_{12}$-$C_{16}$) sulfate | 5 |
| Polyoxyethylene (average number of moles of POE added: 6 to 15) alkyl ($C_{12}$-$C_{18}$) ether | 10 |
| Soap ($C_{14}$-$C_{20}$) | 5 |
| Crystalline alluminosilicate | 25 |
| Sodium carbonate | 15.6 |
| Sodium sulfate | 6 |
| Polyethylene glycol (molecular weight: 8,000-10,000) | 2 |
| Pulverized enzyme | 1 |
| Total | 99.6 |

The invention claimed is:

1. A fragrance composition, comprising synthetic 8-drimanol represented by formula (1a):

(1a)

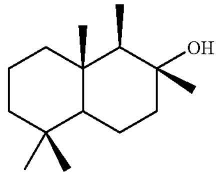

with the proviso that none of 7-acetyl-1,2,3,4,5,6,7,8-octahydro-1,1,6,7-tetramethylnaphthalene, 1,2,3,4,4a,5,6,7-octahydro-2,5,5-trimethyl-2-naphthalenol, 1,2,3,4,4a,7,8,8a-octahydro-2,4a,5,8a-tetramethyl-1-naphthylformate, 3a-ethyldodecahydro-6,6,9a-trimethylnaphtho[2,1-b] furan, racemic dodecahydro-3a,6,6,9a-tetramethylnaphtho[2,1-b]furan, optically-active dodecahydro-3a,6,6,9a-tetramethylnaphtho[2,1-b]furan, and norambreinolide are present in said fragrance composition;

wherein the 8-drimonol imparts the fragrance to the fragrance composition.

2. The fragrance composition according to claim 1, which comprises from 0.0001 to 99 mass % of synthetic 8-drimanol represented by the formula (1a).

3. The fragrance composition according to claim 2, which further comprises one or more compounds selected from the group consisting of methyl dihydrojasmonate, cis-3-hexenyl salicylate, ethylene brassylate, cyclopentadecanolide, 7-hexadecen-16-olide, 2-methyl-4-(2,2,3-trimethyl-3-cyclopenten-1-yl) -2-butene-1-ol, and methyl β-naphthyl ketone.

4. The fragrance composition according to claim 1, which further comprises one or more compounds selected from the group consisting of methyl dihydrojasmonate, cis-3-hexenyl salicylate, ethylene brassylate, cyclopentadecanolide, 7-hexadecen-16-olide, 2-methyl-4-(2,2,3-trimethyl-3-cyclopenten-1-yl)-2-butene-1-ol, and methyl β-naphthyl ketone.

5. A personal care product, comprising the fragrance composition of claim 1.

6. A household product, comprising the fragrance composition of claim 1.

7. An environmental hygiene product, comprising the fragrance composition of claim 1.

8. A method of improving the fragrance of a fragrance composition, which comprises adding synthetic 8-drimanol represented by formula (1a):

(1a)

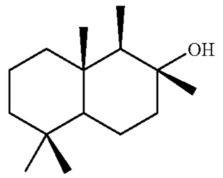

to said fragrance composition with the proviso that none of 7-acetyl-1,2,3,4,5,6,7,8-octahydro-1,1,6,7-tetramethylnaphthalene, 1,2,3,4,4a,5,6,7-octahydro-2,5,5-trimethyl-2-naphthalenol, 1,2,3,4,4a,7,8,8a-octahydro-2,4a,5,8a-tetramethyl-1-naphthylformate, 3a-ethyldodecahydro-6,6,9a-trimethylnaphtho[2,1-b] furan, racemic dodecahydro-3a,6,6,9a-tetramethylnaphtho[2,1-b]furan, optically-active dodecahydro-3a,6,6,9a-tetramethylnaphtho[2,1-b]furan, and norambreinolide are present in said fragrance composition; wherein the 8-drimonol imparts the fragrance to the fragrance composition.

9. A personal care product comprising the fragrance composition of claim 2.

10. A household product comprising the fragrance composition of claim 2.

11. An environmental hygiene product comprising the fragrance composition of claim 2.

12. A method of perfuming an object, comprising applying an effective amount of a fragrance composition of claim 1 to said object.

13. A method of perfuming an object, comprising applying an effective amount of a fragrance composition of claim 2 to said object.

14. A fragrance composition, consisting essentially of synthetic 8-drimanol represented by formula (1a):

(1a)

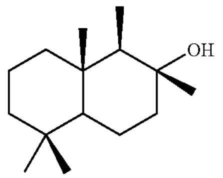

with the proviso that none of 7-acetyl-1,2,3,4,5,6,7,8-octahydro-1,1,6,7-tetramethylnaphthalene, 1,2,3,4,4a,5,6,7-octahydro-2,5,5-trimethyl-2-naphthalenol, 1,2,3,4,4a,7,8,8a-octahydro-2,4a,5,8a-tetramethyl-1-naphthylformate, 3a-ethyldodecahydro-6,6,9a-trimethylnaphtho[2,1-b]furan, racemic dodecahydro-3a,6,6,9a-tetramethylnaphtho[2,1-b]furan, optically-active dodecahydro-3a,6,6,9a-tetramethylnaphtho[2,1-b]furan, and norambreinolide are present in said fragrance composition; wherein the 8-drimonol imparts the fragrance to the fragrance composition.

15. A personal care product comprising the fragrance composition of claim 14.

16. A household product comprising the fragrance composition of claim 14.

17. An environmental hygiene product comprising the fragrance composition of claim 14.

18. A method of perfuming an object, said method comprising applying an effective amount of the fragrance composition of claim 14 to said object.

* * * * *